United States Patent [19]
Roe et al.

[11] Patent Number: 5,776,121
[45] Date of Patent: Jul. 7, 1998

[54] ABSORBENT ARTICLE HAVING INTEGRAL BARRIER CUFFS AND PROCESS FOR MAKING THE SAME

[75] Inventors: Donald Carroll Roe, West Chester; Frank Heinrich Bakes, Cincinnati; Dean Jeffrey Daniels, Cincinnati; Kimberly Ann Dreier, Cincinnati; Michael Thomas Huber, Cincinnati; John Carroll Molander, Montgomery, all of Ohio

[73] Assignee: The Procter & Gamble Company, Cincinnati, Ohio

[21] Appl. No.: 619,112

[22] Filed: Mar. 20, 1996

Related U.S. Application Data

[63] Continuation of Ser. No. 361,248, Dec. 21, 1994, abandoned.

[51] Int. Cl.⁶ .................................................. A61F 13/15
[52] U.S. Cl. ............................................................. 604/385.1
[58] Field of Search .......................... 604/385.1, 385.2

[56] References Cited

U.S. PATENT DOCUMENTS

| | | | |
|---|---|---|---|
| Re. 33,106 | 11/1989 | Beckestrom | 604/385.2 |
| 3,807,402 | 4/1974 | Miller et al. | 128/287 |
| 3,911,173 | 10/1975 | Sprague, Jr. | 427/207 |
| 3,920,017 | 11/1975 | Karami | 128/287 |
| 3,929,135 | 12/1975 | Thompson | 128/287 |
| 4,246,900 | 1/1981 | Schroder | 128/287 |
| 4,341,216 | 7/1982 | Obenour | 128/287 |
| 4,342,314 | 8/1982 | Radel et al. | 128/287 |
| 4,381,782 | 5/1983 | Mazurak et al. | 604/385.2 |
| 4,410,324 | 10/1983 | Sabee | 604/368 |
| 4,463,045 | 7/1984 | Ahr et al. | 428/131 |
| 4,490,148 | 12/1984 | Beckestrom | 604/385 |
| 4,515,595 | 5/1985 | Kievet et al. | 604/385 |
| 4,573,986 | 3/1986 | Minetola et al. | 604/366 |
| 4,610,678 | 9/1986 | Weisman et al. | 604/368 |
| 4,657,539 | 4/1987 | Hasse | 604/385 |
| 4,673,402 | 6/1987 | Weismann et al. | 604/368 |
| 4,681,579 | 7/1987 | Toussant et al. | 604/385 |
| 4,695,278 | 9/1987 | Lawson | 604/385 |
| 4,704,115 | 11/1987 | Buell | 604/385 |
| 4,704,116 | 11/1987 | Enloe | 604/385 |
| 4,738,677 | 4/1988 | Foreman | 604/385 |
| 4,785,996 | 11/1988 | Ziecker et al. | 239/298 |
| 4,795,452 | 1/1989 | Blaney et al. | 604/385.1 |
| 4,795,454 | 1/1989 | Dragoo | 604/385 |
| 4,834,735 | 5/1989 | Alemany et al. | 604/368 |
| 4,842,666 | 6/1989 | Werenicz | 156/161 |
| 4,846,823 | 7/1989 | Enloe | 604/385 |
| 4,846,825 | 7/1989 | Enloe et al. | 604/385.1 |
| 4,888,231 | 12/1989 | Angstadt | 428/213 |
| 4,900,317 | 2/1990 | Buell | 604/370 |
| 4,904,251 | 2/1990 | Igaue et al. | 604/385.2 |
| 4,909,803 | 3/1990 | Ariz et al. | 604/385.2 |
| 4,938,755 | 7/1990 | Foreman | 604/385.2 |
| 4,944,735 | 7/1990 | Mokry | 604/385.2 |

(List continued on next page.)

FOREIGN PATENT DOCUMENTS

| | | | |
|---|---|---|---|
| 4-12751 | 1/1992 | Japan | A61F 13/15 |
| 2161059 | 1/1986 | United Kingdom | A41B 13/02 |
| 9418927 | 1/1994 | WIPO | A61F 13/15 |

*Primary Examiner*—Michael J. Milano
*Attorney, Agent, or Firm*—Larry L. Huston; Edward J. Milbrada; J. Daniel Lykins

[57] ABSTRACT

Absorbent articles, such as disposable diapers, having two waist regions and a crotch region are provided. The absorbent articles comprise a liquid pervious topsheet, a liquid impervious backsheet, an absorbent core disposed between the topsheet and the backsheet, and a pair of longitudinally extending barrier cuffs. The barrier cuffs are formed from a lateral extension of the topsheet and the backsheet in at least the crotch region of the absorbent article using material that is normally discarded when the crotch area is formed. A cuff area is defined by pairs of laterally opposed cuts in the lateral extension of the topsheet and the backsheet. The cuff area is then folded and joined to the topsheet or other underlying structure to form the barrier cuff and an optional gasketing cuff.

17 Claims, 7 Drawing Sheets

U.S. PATENT DOCUMENTS

| | | | |
|---|---|---|---|
| 5,021,051 | 6/1991 | Hiuke | 604/385.2 |
| 5,032,120 | 7/1991 | Freeland et al. | 604/385.2 |
| 5,085,654 | 2/1992 | Buell | 604/370 |
| 5,087,255 | 2/1992 | Sims | 604/385.1 |
| 5,114,420 | 5/1992 | Igaue et al. | 604/385.2 |
| 5,151,092 | 9/1992 | Buell et al. | 604/385.2 |
| 5,167,653 | 12/1992 | Igaue et al. | 604/385.2 |
| 5,190,606 | 3/1993 | Merkatoris et al. | 156/164 |
| 5,254,111 | 10/1993 | Cancio et al. | 604/385.1 |
| 5,306,268 | 4/1994 | Enloe | 604/385.2 |
| 5,318,554 | 6/1994 | Young et al. | 604/378 |
| 5,536,350 | 7/1996 | Klemp | 156/211 |

ABSORBENT ARTICLE HAVING INTEGRAL BARRIER CUFFS AND PROCESS FOR MAKING THE SAME

This is a continuation of application Ser. No. 08/361,248, filed Dec. 21, 1994 now abandoned.

FIELD OF THE INVENTION

The present invention relates to absorbent articles such as disposable diapers, and more particularly, to absorbent articles having integral barrier cuffs formed from portions of the web from which the article is cut which previously would have been removed to form the leg openings or notches and discarded as scrap.

BACKGROUND OF THE INVENTION

The primary function of absorbent articles such as disposable diapers and incontinence briefs or undergarments is to absorb and contain body exudates. Such articles are thus intended to prevent body exudates from soiling, wetting, or otherwise contaminating clothing or other articles, such as bedding, that come in contact with the wearer. The most common mode of failure for such products occurs when body exudates leak out of the gaps between the article and the wearer's leg or waist onto adjacent clothing because they are not immediately absorbed within the article or the absorbent article is not able to sustain a good fit on the wearer such that gaps are created allowing the exudates to leak out of the absorbent article. For example, urine tends to be deposited onto the topsheet in gushes such that the urine migrates to the gaps in the chassis faster than it can be absorbed and such that it can come in contact with clothing or other articles and be absorbed by these articles. Additionally, loose fecal material that is not easily absorbed by the absorbent article tends to "float" on the liquid-receiving surface and work its way past the gaps in the article in the legs or waist of the wearer.

Contemporary disposable diapers have a fluid pervious topsheet, a fluid impervious backsheet, an absorbent core, and elasticized leg flaps generally formed from an elastic member being enclosed in the continuous topsheet and backsheet which extend beyond the edges of the absorbent core. These elasticized leg flaps prove efficient generally to prevent wicking and overflow from the fluid laden diaper to clothing contacting the edges of the diaper since the elasticized leg flaps present a fluid impervious barrier between the edge of the diaper and clothing, and in addition, provide a gasketing action about the legs of the wearer to maintain a seal about the leg and minimize gapping. However, leakage along the perimeter of the diaper may still occur. As the diaper is worn for longer periods of time, forces tend to act on the diaper to degrade the initial fit on the wearer. Large gaps and sagging of the diaper in the legs and waist result in the degradation in fit. Thus, as liquids are deposited onto the topsheet, some of the liquid is not immediately absorbed through the topsheet and migrates toward the edges of the diaper where it can leak through or past the gaps in the diaper and come in contact with clothing or undergarments where it can be absorbed by and wicked into such garments.

Disposable diapers have been provided with separately attached barrier cuffs which inhibit loose fecal material or gushes of urine or liquids from soiling the wearer's clothing. The barrier cuffs restrain the free flow of this material and provide a structure to hold such material within the diaper so that as such material freely floats or flows on the topsheet of the diaper, it is contained within the diaper. Typically, the barrier cuffs are formed by attaching an independent web of cuff material to the topsheet web or to the topsheet of a completed chassis. For example, commonly assigned U.S. Pat. No. 4,695,278 to Lawson teaches a dual cuff arrangement in which the barrier cuff is a separate element joined to the topsheet. When the barrier cuff is attached to the topsheet as a separate element, special machinery dedicated to attaching the barrier cuffs is required and, consequently, the extra machinery increases the cost of the completed article.

Furthermore, when conventional diapers are manufactured, notches are cut in the sides of the article to provide a contour for the legs of the person who will wear the article. For example, leg notches account for approximately 15–20% of the area of an absorbent article. The portion removed from the article to create the leg notches has no further use in the manufacturing process and is discarded. Thus, the current methods of manufacturing diapers produce a large volume of unnecessary waste.

SUMMARY OF THE INVENTION

This invention relates to a disposable absorbent article having barrier cuffs and a method for making that article. The cuffs are integral with the diaper, i.e., they are not separately formed and then attached to the article. The article includes a chassis which consists of a fluid pervious topsheet, a fluid impervious backsheet, and an absorbent core disposed between the topsheet and backsheet.

In a first embodiment, the barrier cuffs are formed from an extension of the topsheet and backsheet beyond the longitudinal edges of the absorbent core and have a first and second end which are attached to the topsheet or other underlying layer of the diaper. The barrier cuffs are formed from a cuff area defined by cuts in the diaper web. The barrier cuffs are formed by folding the cuff area toward the longitudinal centerline of the absorbent article and attaching at least a portion of the cuff area adjacent the ends of the cuff area to the topsheet. The barrier cuffs further include a spacing means to space the cuffs away from the chassis at least in the crotch region of the article. As a modification to this embodiment, the article may further include gasketing cuffs which are also formed from the extended topsheet and backsheet material.

In a second embodiment, the article includes barrier cuffs which each consist of one layer of topsheet and one layer of backsheet and gasketing cuffs which each consist of two layers of topsheet sandwiched between two layers of backsheet material. The barrier cuffs and the gasketing cuffs are formed from a cuff area defined by cuts in the diaper web. The cuffs are formed by one of the folding patterns described below. The barrier cuffs of this invention also preferably include a spacing means, which is preferably elastic, to space the cuffs away from the chassis and, preferably, the gasketing cuffs will include an elasticized member.

In a third embodiment, the barrier cuffs each consist of two layers of backsheet material sandwiched between two layers of topsheet material and the gasketing cuffs each consist of a single layer of topsheet material and backsheet material. The barrier cuffs and the gasketing cuffs are also formed from the cuff area described above. The cuffs are then formed by another of the folding patterns described below. Again, the barrier cuffs include a spacing means and, preferably, the gasketing cuffs also include an elasticized member.

The process, by which the absorbed articles of this invention are made, begins with a web having longitudinal edges which consists of topsheet, backsheet and absorbent cores disposed between the topsheet and the backsheet. The web is ultimately laterally severed at spaced apart intervals to form individual absorbent articles. Each absorbent article has a first waist region, a second waist region, a crotch region located between the first and second waist regions, longitudinal and lateral centerlines, longitudinal edges and end edges.

To define barrier cuffs and gasketing cuffs, the web is first cut at spaced apart intervals along each longitudinal edge to define a cuff area having inner, outer and middle longitudinal portions. The cuff area is then folded to form the leg cuffs, as described below. The cuts are provided in either the first waist region, the second waist region, or both the first and second waist regions. The articles are preferably folded according to one of the three following folding patterns.

In a first folding pattern according to this invention, cuts are provided in both the first waist region and the second waist region on each side of the article. These cuts define a cuff area which is folded toward the longitudinal centerline of the absorbent article to form a barrier cuff and a gasketing cuff. Once the cuff areas have been folded, a portion of the cuff area adjacent each of the ends of the cuff area are attached to the topsheet or a layer which underlies the topsheet of the article in both the first and second waist regions to complete the barrier cuffs and gasketing cuffs.

In a second folding pattern according to this invention, cuts are provided as described above, a bonding means is provided to the cuff area longitudinally adjacent either side of a line connecting the closed ends of the cuts (i. e. that end of the cut closest to the longitudinal centerline of the absorbent article). The cuff area is folded toward the longitudinal centerline. The bonding means secures a portion of the cuff area to the topsheet or a layer which underlies the topsheet in at least the crotch region of the resulting article. Once secured, the cuff is then folded away from the longitudinal centerline to produce the barrier cuff. The ends of the barrier cuffs are attached to the topsheet or a layer which underlies the topsheet in the first and second waist regions of the article so that a barrier cuff having a distal edge which is free from the topsheet at least in the crotch region results. The portion of the cuff areas longitudinally adjacent to the longitudinal edges forms a gasketing cuff. The resulting barrier cuffs each consist of one layer of topsheet and one layer of backsheet and the outer gasket cuff comprises two layers of backsheet and two layers of topsheet material.

In a third folding pattern, a first bonding means is provided to the topsheet in the first and second waist regions. The cuff area is first folded toward the longitudinal centerline and joined to the underlying elements in the first and second waist regions. After the cuff area is folded toward the longitudinal centerline, a second bonding means is provided to the garment facing surface of the cuff area preferably in its middle longitudinal portion and a third bonding means is provided to the body facing surface of the cuff area in the first and second waist regions of the article along the cut lines. The cuff area is then folded away from the longitudinal centerline so that the cuff area becomes attached to itself in its middle longitudinal portion. The cuff is then attached to the topsheet in the first and second waist regions to produce a barrier cuff having two layers of backsheet material and two layers of topsheet material and a gasketing cuff having only a single layer of topsheet and backsheet material.

BRIEF DESCRIPTION OF THE DRAWINGS

While the specification concludes with claims particularly pointing out and distinctly claiming the subject matter which is regarded as forming the present invention the invention will be explained by reference to the following descriptions which are taken in conjunction with the accompanying drawings in which like designations are used to designate substantially identical elements, and in which:

DETAILED DESCRIPTION OF THE INVENTION

Figure 1:
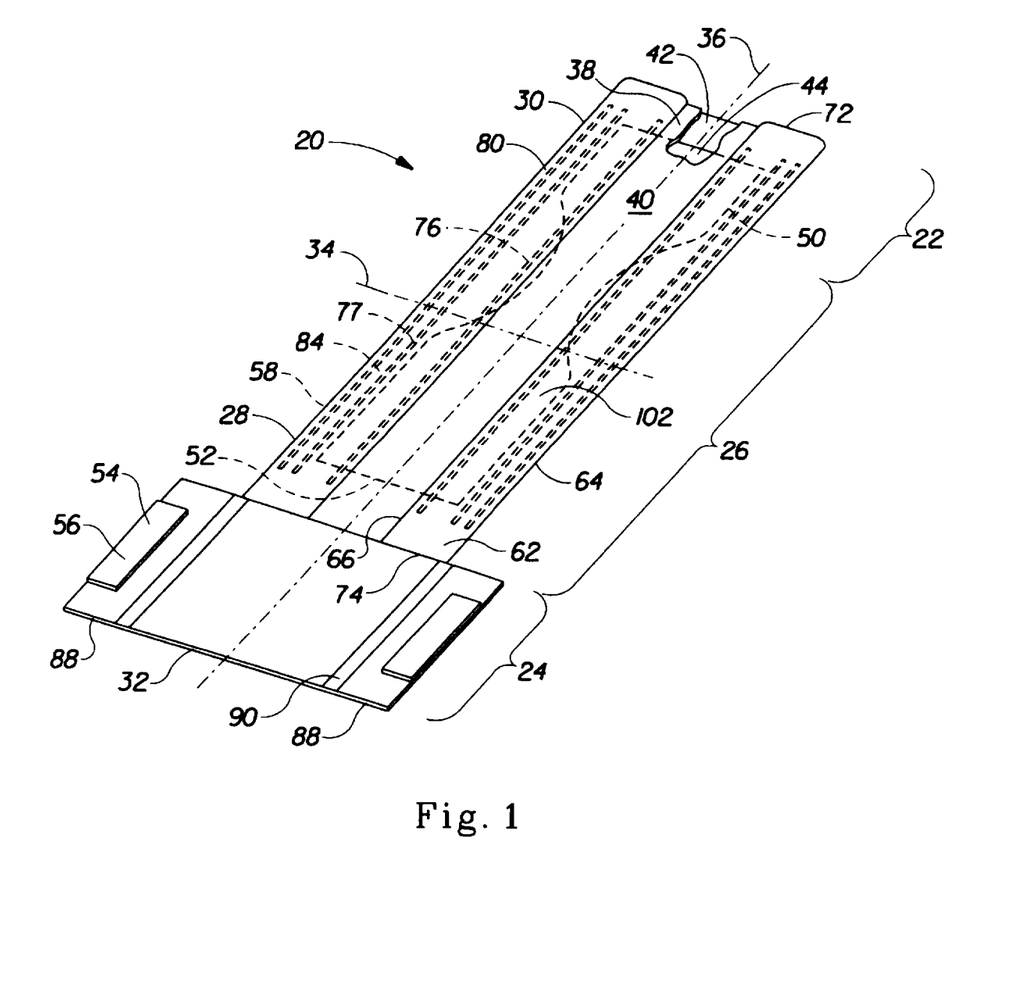
FIG. 1 is a plan view of an absorbent article having integral barrier cuffs formed by the process of this invention.

The Product:

As used herein, the term "absorbent article" refers to articles which absorb and contain body exudates and more specifically refers to articles which are placed against or in proximity to the body of the wearer to absorb and contain the various exudates discharged from the body. Absorbent articles are typically differentiated by whether they are reusable or disposable. Disposable absorbent articles are those articles which are intended to be discarded after a single use (i.e., they are not intended to be laundered or otherwise restored or reused). The absorbent articles of the present invention are preferably disposable absorbent articles. The absorbent articles may be further defined by whether they are "unitary" such that they do not require separate manipulative parts or whether they comprise a detached element of a diaper system such as a separate holder and liner. The absorbent articles of the present invention are preferably unitary. An embodiment of the present invention, a diaper 20, is shown in FIG. 1. As used herein, the term "diaper" refers to a garment generally worn by infants and incontinent persons that is worn about the lower torso of the wearer. It should be understood, however, that the present invention is also applicable to other disposable absorbent articles such as incontinence briefs or undergarments, disposable training pants, diaper holders, sanitary napkins, and the like.

FIG. 1 is a plan view of an absorbent article, diaper 20, of the present invention in its flat-out, uncontracted state (i.e., with all elastic induced contraction pulled out) with portions of the structure being cut-away to more clearly show the construction of the diaper 20 and with the portion of the diaper 20 which contacts the wearer oriented toward the viewer. The diaper 20 is shown in FIG. 1 to have a first waist region 22, a second waist region 24, a crotch region 26, and a periphery 28 which is defined by the outer edges of the diaper 20 in which the longitudinal edges are designated 30 and the end edges are designated 32. The diaper 20 additionally has a lateral centerline which is designated 34 and a longitudinal centerline which is designated 36.

The diaper 20 comprises a liquid pervious topsheet 38, a body facing surface 40 generally defined by the topsheet 38; a liquid impervious backsheet 42; a garment facing surface 58 generally defined by the backsheet 42, an absorbent core 44; fastening means 54 for securing the diaper 20 on the wearer such as the pair of tape tab fasteners 56; barrier cuffs 62 each having a proximal edge 64, a distal edge 66, a first end 72, and a second end 74; spacing means 76 such as elastic members 77 for spacing the distal edge 66 away from the body facing surface 40; ear panels 88; and an elastic waist feature 90.

FIG. 1 shows an embodiment of the diaper 20 in which the topsheet 38 and backsheet 42 have length and width dimensions generally larger than those of the absorbent core 44. The topsheet 38 and backsheet 42 extend beyond the edges of the absorbent core 44 to thereby form the periphery 28 of the diaper 20. The periphery 28 comprises the longitudinal edges 30 and the end edges 32. As shown in FIG. 1, the topsheet 38 is generally coterminous with the backsheet 42 along at least the end edges 32 and preferably the longitudinal edges 30. While the topsheet 38, backsheet 42 and absorbent core 44 may be assembled in a variety of well known configurations, preferred diaper configurations are generally described in U.S. Pat. No. 3,860,003 entitled "Contractible Side Portions for Disposable Diaper" to Kenneth Buell; and U.S. Pat. No. 5,151,092 entitled, "Absorbent Article with Dynamic Elastic Waist Feature Having a Predisposed Resilient Flexural Hinge", to Buell et al.; each of which is incorporated herein by reference.

The diaper 20 has two longitudinally opposed waist regions, first waist region 22 and a second waist region 24 extending, respectively, from the end edges 32 of the diaper periphery 28 toward the lateral centerline 34 of the diaper 20. The waist regions 22 and 24 generally comprise those portions of the diaper 20 which, when worn, encircle the waist of the wearer. The crotch region 26 is that portion of the diaper 20 positioned between the first waist region 22 and the second waist region 24, and comprises that portion of the diaper 20 which, when worn, is positioned between the legs of the wearer and covers the lower torso of the wearer.

The absorbent core 44 may be any means which is generally compressible, conformable, non-irritating to the wearer's skin, and capable of absorbing and retaining liquids and certain body exudates. The absorbent core has longitudinal sides 50 and lateral ends 52. The absorbent core 44 may be manufactured in a wide variety of sizes and shapes (e.g., rectangular, hour-glass, asymmetric, etc.) and from a wide variety of liquid absorbent materials commonly used in disposable diapers and other absorbent articles, such as comminuted wood pulp which is generally referred to as air-felt. Examples of other suitable absorbent materials include creped cellulose wadding, absorbent foams, absorbent sponges, super absorbent polymers, absorbent gelling materials, or any equivalent materials or combination of materials. The configuration and construction of the absorbent core may also be varied (e.g., the absorbent core may have varying caliper zones, a hydrophilic gradient, a super-absorbent gradient, or lower average density and lower average basis weight acquisition zones; or may comprise one or more layers or structures). The total absorbent capacity of the absorbent core 44 should, however, be compatible with the design loading and the intended use of the diaper 20. Further, the size and absorbent capacity of the absorbent core 44 may be varied to accommodate wearers ranging in size from infants through adults. Exemplary absorbent structures for use as the absorbent core 44 are described in U.S. Pat. No. 4,610,678 entitled "High-Density Absorbent Structures" issued to Weisman et al. on Sep. 9, 1986; U.S. Pat. No. 4,673,402 entitled "Absorbent Articles With Dual-Layered Cores" issued to Weisman et al. on Jun. 16, 1987; U.S. Pat. No. 4,888,231 entitled "Absorbent Core Having a Dusting Layer" issued to Angstadt on Dec. 19, 1989; U.S. Pat. No. 4,834,735 entitled "High Density Absorbent Members Having Lower Density and Lower Basis Weight Acquisition Zones", issued to Alemany et al. on May 30, 1989; and U.S. Pat. No. 5,318,554 to Young, et al. on Jun. 7, 1994. Each of these patents are incorporated herein by reference.

The backsheet 42 is positioned adjacent the absorbent core 44 and is preferably secured by core attachment means (not shown) such as those well known in the art. For example, the backsheet 42 may be secured to the absorbent core 44 by a uniform continuous layer of adhesive, a patterned layer of adhesive, or an array of separate lines or spots of adhesive. Adhesives which have been found to be satisfactory are manufactured by H. B. Fuller Company of St. Paul, Minn. and marketed as HL-1258. The attachment means will preferably comprise an open pattern network of filaments of adhesive as is disclosed in U.S. Pat. No. 4,573,986 entitled "Disposable Waste-Containment Garment", which issued to Minetola, et al. on Mar. 4, 1986, more preferably several lines of adhesive filaments swirled into a spiral pattern such as is illustrated by the apparatus and methods shown in U.S. Pat. No. 3,911,173 issued to Sprague, Jr. on Oct. 7, 1975; U.S. Pat. No. 4,785,996 issued to Ziecker, et al. on Nov. 22, 1978; and U.S. Pat. No. 4,842,666 issued to Werenicz on Jun. 27, 1989. Each of these patents are incorporated herein by reference. Alternatively, the attachment means may comprise heat bonds, pressure bonds, ultrasonic bonds, dynamic mechanical bonds, or any other suitable attachment means or combinations of these attachment means as are known in the art.

The backsheet 42 is impervious to liquids and is preferably manufactured from a thin plastic film, although other flexible liquid impervious materials may also be used. As used herein, the term "flexible" refers to materials which are compliant and will readily conform to the general shape and contours of the human body. The backsheet 42 prevents the exudates absorbed and contained in the absorbent core 44 from wetting articles which contact the diaper 20 such as bed sheets and clothing. The backsheet 42 may thus comprise a woven or non-woven material, polymeric films such as thermoplastic films of polyethylene or polypropylene, or composite materials such as a film-coated non-woven material. Preferably, the backsheet is a thermoplastic film having a thickness of from about 0.012 mm (0.5 mil) to about 0.051 mm (2.0 mils). Particularly preferred materials for the backsheet include RR8220 blown films and RR5475 cast films as manufactured by Tredegar Industries, Inc. of Terre Haute, Ind. and P18-1401 available from Clopay Corp. of Cincinnati, Ohio. The backsheet 42 is preferably embossed and/or matte finished to provide a more cloth-like appearance. Further, the backsheet 42 may permit vapors to escape from the absorbent core 44 (i.e., breathable) while still preventing exudates from passing through the backsheet 26. The size of the backsheet 42 is dictated by the size of the absorbent core 44 and the exact diaper design selected.

The topsheet 38 is positioned adjacent the body facing surface of the absorbent core 44 and is preferably joined thereto and to the backsheet 42 by attachment means (not shown) such as those well known in the art. Suitable attachment means are described with respect to joining the backsheet 42 to the absorbent core 44. As used herein, the term "joined" encompasses configurations whereby an element is directly secured to the other element by affixing the element directly to the other element, and configurations whereby the element is indirectly secured to the other element by affixing the element to intermediate member(s) which in turn are affixed to the other element. In a preferred embodiment of the present invention, the topsheet 38 and the backsheet 42 are joined directly to each other in the diaper periphery 28 and are indirectly joined together by directly joining them to the absorbent core 44 by the attachment means (not shown).

The topsheet 38 is compliant, soft feeling, and non-irritating to the wearer's skin. The topsheet 38 is liquid pervious in at least those portions overlying the absorbent core 44 permitting liquids (e.g. urine) to readily penetrate through its thickness. A suitable topsheet may be manufactured from a wide range of materials, such as porous foams, reticulated foams, apertured plastic films, natural fibers (e.g., wood or cotton fibers), synthetic fibers (e.g. polyester or polypropylene fibers) or from a combination of natural and synthetic fibers. If the topsheet 38 is made of a hydrophobic material, at least the upper surface of the topsheet 38 is treated to be hydrophilic in that portion of the topsheet that is intended to receive liquids so that liquids will transfer through the topsheet more rapidly. This diminishes the likelihood that body exudates will flow off the topsheet 38 rather than being drawn through the topsheet 38 and being absorbed by the absorbent core 44. Preferred embodiments of the topsheet 38 are also hydrophobic in at least the cuff area 102. Preferably all portions of the topsheet 38 lying laterally outboard of longitudinal edge of the absorbent core 44 are hydrophobic. As used herein, the term "hydrophobic" is intended to mean that the topsheet 48 is not wetted by aqueous liquids.

There are a number of manufacturing techniques which may be used to manufacture the topsheet 38. For example, the topsheet 38 may be woven, non-woven, spunbonded, carded, or the like. A preferred topsheet 38 is carded, and thermally bonded by means well known to those skilled in the fabrics art. Alternatively, the topsheet 38 may be an apertured formed film as described in U.S. Pat. No. 4,463,405 to Ahr et al. entitled "Macroscopically Expanded Three-Dimensional Plastic Web Exhibiting Non-Glossy Visible Surface and Cloth-Like Tactile Impression"; U.S. Pat. No. 4,432,312 to Radel et al. entitled "Resilient Plastic Web Exhibiting Fiber-Like Properties"; and U.S. Pat. No. 3,929,135 to Thompson entitled "Absorptive Structure Having Tapered Capillaries"; all of which are herein incorporated by reference. A preferred topsheet comprises a web of staple length polypropylene fibers such as is manufactured by Veratec, Inc., a Division of the International Paper Company of Walpole, Mass. under the Product designation P 8. Preferably, the topsheet 38 has a weight from about 14 to about 25 grams per square meter, a minimum dry tensile strength of at least about 400 grams per centimeter in the longitudinal direction and a wet tensile strength of at least about 55 grams per centimeter in the lateral direction.

The diaper 20 preferably includes ear panels 88 which are that portion of the diaper 20 which extend laterally outwardly from a line parallel to the longitudinal edge of the absorbent core 44 to the lateral edge of the diaper 20 in at least one of the waist regions 22 or 24. The ear panels 88 generally extend longitudinally from the end 32 of the diaper 20 toward the absorbent core in at least one of waist regions 22, 24. In the embodiment shown in FIG. 1, the ear panels 88 are located in the second waist regions 24. The ear panels 88 are formed from the portion of the topsheet 38 and the backsheet 42 that extend beyond the laterally side edge of the absorbent core 44 in the second waist region 24. Preferably, the ear panels 88 further comprise an elastic member(not shown) disposed between the extended topsheet and backsheet and are mechanically prestrained as described in the above referenced U.S. Pat. No. 5,151,092 which is incorporated herein by reference.

The diaper 20 preferably further comprises an elastic waist feature 90 that provides improved fit and containment. The elastic waist feature 90 is that portion or zone of the diaper 20 which is intended to elastically expand and contract to dynamically fit the wearer's waist. The elastic waist feature extends longitudinally outwardly from at least one of the end edges of the absorbent core 44 and generally forms at least a portion of the end edge 32 of the diaper 20. Disposable diapers are frequently constructed so as to have two elastic waist features, one positioned in the first waist region 22 and one positioned in the second waist region 24, although diapers can be constructed with a single elastic waist feature located in either the first waist region 22 or the second waist region 24. In the embodiment shown in FIG. 1, the elastic waist feature 90 is operatively associated with the ear panels 88 in second waist region 24. Further, while the elastic waist feature 90 or any of its constituent elements can comprise a separate element affixed to the diaper 20, the elastic waist feature 90 is preferably constructed as an extension of other elements of the diaper such as the backsheet 42 or the topsheet 38, preferably both the backsheet 42 and the topsheet 38. The elastic waist feature 90 may be constructed in a number of different configurations including those described in U.S. Pat. No. 4,515,595 issued to Kievit et al. on May 7, 1985 and the above referenced U.S. Pat. No. 5,151,092; each of these references being incorporated herein by reference.

Alternatively, the ear panels 88 and/or the waist feature 90 may comprise a structural elastic-like film (SELF) web. A structural elastic-like film web is an extensible material that exhibits an elastic-like behavior in the direction of elongation without the use of added elastic materials. The SELF web includes a strainable network having at least two contiguous, distinct, and dissimilar regions. One of the regions is configured so that it will exhibit resistive forces in response to an applied axial elongation in a direction parallel to predetermined axis before a substantial portion of the other region develops significant resistive forces to the applied elongation. At least one of the regions has a surface-path length which is greater than that of the other region as measured substantially parallel to the predetermined axis while the material is in an untensioned condition. The region exhibiting the longer surface-pathlength includes one or more deformations which extend beyond the plane of the other region. The SELF web exhibits at least one predetermined axis when subjected to an applied elongation in a direction parallel to the predetermined axis. The SELF web exhibits first resistive forces to the applied elongation until the elongation of the web is sufficient to cause a substantial portion of the region having the longer surface-pathlength to enter the plane of applied elongation, whereupon the SELF web exhibits second resistive forces to further elongation. The total resistive forces to elongation are higher than the first resistive forces to elongation provided by the first region. SELF webs suitable for the present invention are more completely described in the copending, commonly assigned U.S. patent application Ser. No. 08/203,456 entitled "Absorbent Article with Multiple Zone Structural Elastic-Like Film Web Extensible Waist Feature" filed by Donald C. Roe, et al. on Feb. 24, 1994, which is incorporated herein by reference.

The diaper 20 is preferably provided with a fastening means 54 for forming a side closure in the diaper 20. Thus, the first waist region 22 and the second waist region 24 are maintained in an overlapping configuration when the diaper 20 is worn. The fastening means 54 may comprise any of a number of fastening systems as are known in the art such as belts, inner fastening members, tape tabs, a hook and loop fastener or other mechanical fasteners.

The barrier cuffs 62 provide a structure to restrain the free flow of body exudates along the body facing surface 40 and to hold and contain such exudates within the diaper 20 and to help provide a gasketing action about the wearer. Each barrier cuff 62 is a flexible member having a proximal edge 64 and a distal edge 66. In addition, the barrier cuff 62 may be provided with a spacing means 76 for spacing the distal edges 66 away from the body facing surface 40 to form a channel (not shown). The spacing means 76 may comprise one or more elastic members 77

As shown in FIG. 1, the barrier cuff 62, and more particularly, the proximal edge 64, includes the longitudinal edge 30 of the diaper 20. The proximal edge 64 is juxtaposed on the longitudinal edge 30 so that exudates, especially loose fecal material which is not easily absorbed and tends to float along the body facing surface 40, will contact the barrier cuff 62 before it can flow out of the diaper 20. It should be noted that if the cuff area is elasticized by one or more elastic members to create an elasticized gasketing cuff, then the proximal edge 64 preferably extends upwardly from the elasticized portion of the gasketing cuff in at least the crotch region 26.

The proximal edges 64 and the distal edges 66 are in a spaced relation to each other and define the effective height of the barrier cuff 62. The proximal edge 64 may be spaced from the distal edge 66 in a parallel and rectilinear relationship. The effective height of the barrier cuff 62 is an important parameter in reducing leakage of body exudates out of the diaper 20. If the effective height of the barrier cuff 62 is too small, then gaps will be formed between the leg of the wearer and the distal edge 66 such that liquids may flow over the distal edge 66 to the periphery 28 of the diaper 20. The effective height of the barrier cuff 62 depends on the specific design chosen for the diaper 20. The effective height of the barrier cuffs 62 is defined as the distance between the longitudinal edge of the core 50 and the distal edge of the barrier cuff 66. For example, for the embodiment shown in FIG. 1, the effective height is at least greater than about 7.6 cm (3.0 in.) and preferably greater than about 8.9 cm (3.5 in.).

The portion of the cuff area adjacent the cuff ends are joined to the topsheet 38 or other underlying structure in the first and second waist regions 22, 24. The distal edge 66 of each barrier cuff 62 is preferably not secured to any underlying elements of the diaper 20 in at least the crotch region 26 so that it may be spaced away from the body facing surface 40. The distal edge 66 is spaced away from the body facing surface 40 so that the barrier cuff 62 may form a channel to enhance the containment of the diaper 20. As used herein, "spaced" includes embodiments wherein the distal edges 66 may assume one or more positions relative to the body facing surface 40 including at some times assuming a position adjacent the body facing surface 40.

A channel (not shown) is preferably formed between the proximal edge 64 and the distal edge 66 of the barrier cuff 62 in at least the crotch region 26. The channel forms a barrier to the flow of exudates as they tend to move or float across the topsheet 38. The channel also contains and holds exudates within the diaper 20 until the diaper 20 can be removed.

A spacing means 76 for spacing the distal edge 66 away from the body facing surface 40 may be any member which gathers, contracts, stiffens, shortens or otherwise acts on the barrier cuff 62 so as to cause the barrier cuffs 62 to stand up to provide a channel along the barrier cuff 62 that acts as a constraint against the leakage of exudates.

As shown in FIG. 1, the spacing means 76 preferably comprises at least one elastic member 77 operatively associated with each of the barrier cuffs 62 adjacent the distal edge 66. A second elastic member 84 may also be provided adjacent the longitudinal edge 30 to form a gasketing cuff 80. The elastic members 77 are preferably secured to the cuff area 102 in an elastically contractible condition so that when the barrier cuffs 62 have been formed, the elastic members 77 effectively contract or gather the distal edge 66 of the barrier cuff 62. The elastic members 77 can be secured to the cuff areas 102 in an elastically contractible condition in at least two ways as is discussed in U.S. Pat. No. 3,860,003, incorporated by reference above, and U.S. Pat. No. 4,695,278 to Lawson entitled "Absorbent Article Having Dual Cuffs", which is incorporated by reference herein. In addition, the length of the elastic member 77 in general is dictated by the diaper design.

Figure 5A:
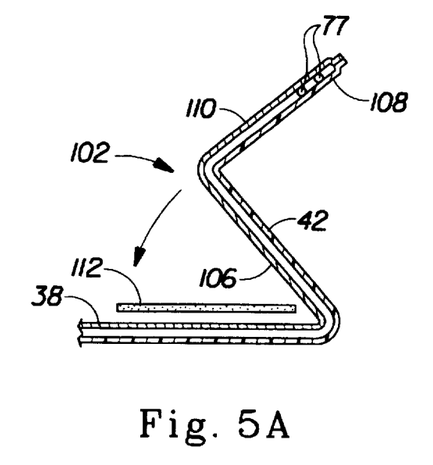
FIGS. 5A and 5B present a partial cross section of the cuff area to illustrate one of the folding patterns of this invention.
Figure 5B:
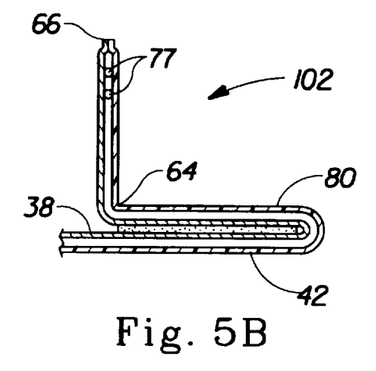
Figure 6A:
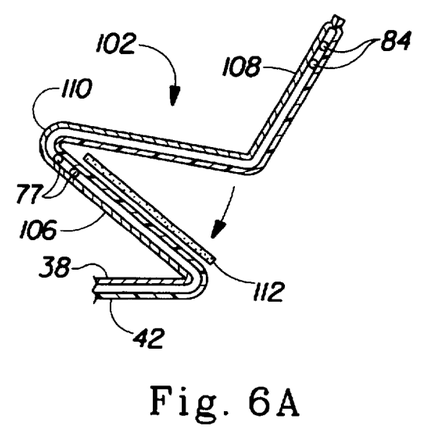
FIGS. 6A and 6B present a partial cross section of the cuff area to illustrate another of the folding patterns of this invention.
Figure 6B:
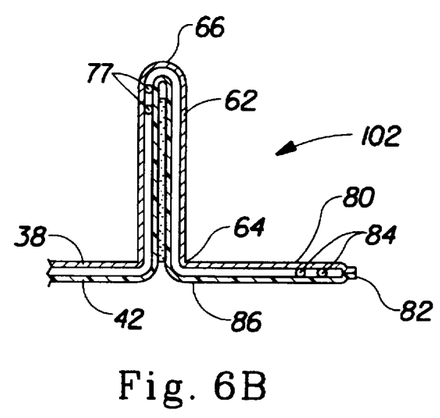

As shown in FIGS. 1, 5B, 6B, and 7, the diaper 20 may also include gasketing cuffs 80. The gasketing cuffs 80 provide a structure to restrain the free flow of body exudates out of the edges of the diaper 20 which contact the legs of the wearer. As shown in FIGS. 5B and 6B, each gasketing cuff 80 is a flexible member having a proximal edge 86 and a distal edge 82. The gasketing cuffs 80 preferably include elastic elements 84 in their distal edges 82 to increase the gasketing action of the gasketing cuffs 80.

Figure 2:
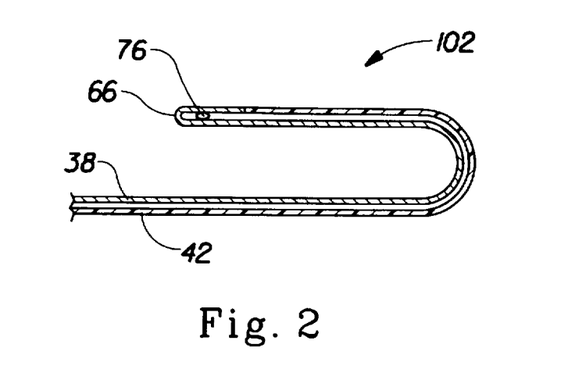
FIG. 2 presents a partial cross section of the cuff area to illustrate one of the folding patterns of this invention.

A preferred embodiment of the diaper 20 shown in FIG. 1 has a backsheet 42 that has a smaller lateral width (i.e., narrower) than the topsheet 38 so the topsheet 38 extends laterally beyond the backsheet in at least the cuff area 102. Further, the spacing means 76 comprises a longitudinally extending elastic member that is wrapped by the extended topsheet in a C-fold to form the distal edge 66 of barrier cuff 62. The cuff area 102 is folded toward the longitudinal centerline 36 and the first and second ends of the cuff area are joined to the topsheet 38 or to other underlying structure in the first and second waist regions 22, 24 as described above. This embodiment is shown in partial cross-section in FIG. 2.

In yet another embodiment of the diaper 20 shown in FIG. 1, the cuff area 102 is folded toward the longitudinal centerline 36 in a first C-fold and the ends of the cuff area are joined to the topsheet or other underlying structure in the first and second waist regions as described above. However, in this embodiment, the ends of the cuff area are joined to the first and second waist areas inboard of the distal edge 66 leaving a portion of the cuff area 102 unattached. This unattached portion is folded away from the longitudinal centerline 36 in a second C-fold and the first and second ends of this unattached portion of the cuff area 102 are joined to underlying structure in the first and second waist regions 22, 24 respectively. This embodiment is shown in partial cross-section in FIG. 3. This embodiment has the advantage of providing a greater effective cuff height without a high risk of blocking those portions of diaper 20 intended to receive bodily exudates.

In the embodiment of this invention shown in FIG. 1, the barrier cuffs 62 are formed by making cuts in the first waist region 22 and the second waist region 24. The cuts in first waist region 22 are preferably made conterminous with the lateral edge 32 of the diaper 20 in that waist region. In this embodiment, the cuts in the second waist region 24 could also comprise a line of weakness such as the land areas of a perforation pattern. The cuts define a cuff area 102 which is folded toward the longitudinal centerline 36 to form the barrier cuff 62. As described above, at least the distal edge 66 and, preferably, that portion of the cuff area 102 in the first and second waist regions 22 and 24, is attached to the topsheet 38 or a layer underlying the topsheet 38 in the first waist region 22 and the second waist region 24. The barrier cuff 62 includes a spacing means which keeps the distal edge 66 of the cuff 62 remote from the diaper 20 in at least the crotch region 26. Preferably, the spacing means 76 is elastic.

Figure 4:
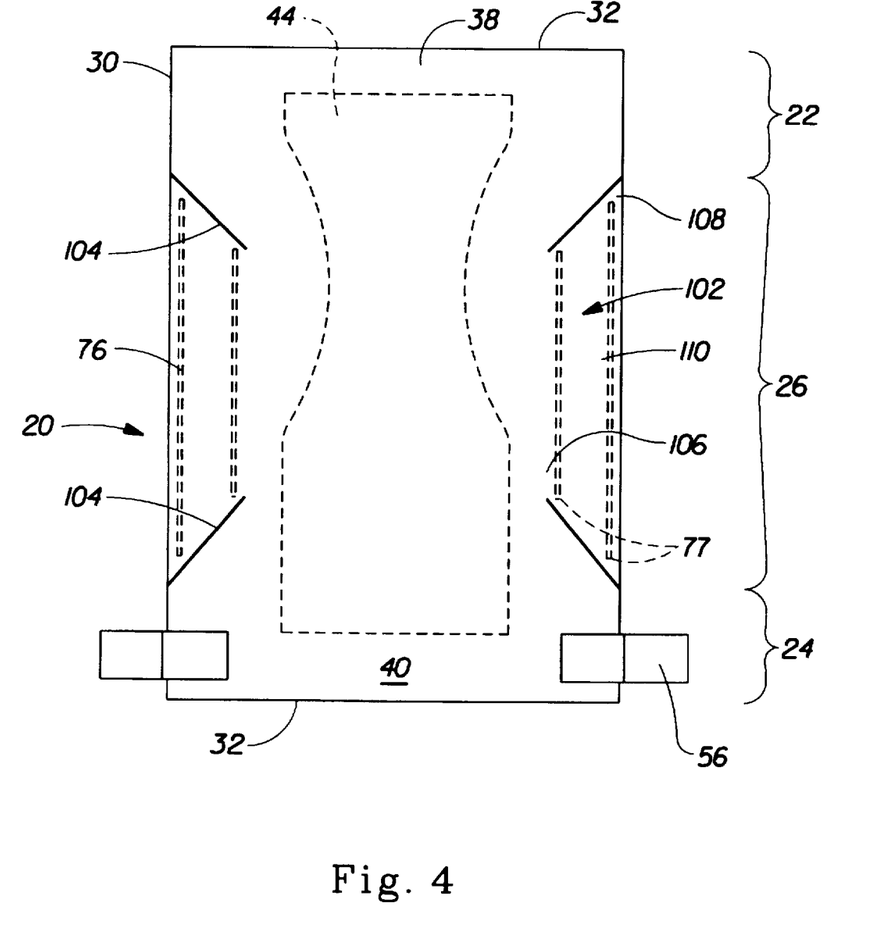
FIG. 4 presents an illustration of the article of an alternative embodiment before the folding process takes place.

In an alternate embodiment of the diaper 20, as shown in FIG. 4, the cuff area 102 is formed by making two cuts on each longitudinal side 30 of the diaper 20. The cuff area 102 is then folded using one of the folding patterns described below to produce a barrier cuff 62 and a gasketing cuff 80. The cuff areas 102 of this embodiment may be folded in a variety of ways.

In one folding pattern shown in FIGS. 5A and 5B, the cuff area is folded as shown and bonding means 112 provided to join the inner longitudinal portion 106 to the topsheet 38 or other underlying layers. The resulting barrier cuff 62 comprises one layer of topsheet 38 and one layer of backsheet 42 and the resulting gasketing cuff 80 comprises two layers of topsheet 38 sandwiched between two layers of backsheet 42. In a second folding pattern shown in FIGS. 6A and 6B the middle longitudinal portion is divided into two subportions by a fold line and the bonding means 112 joins the garment facing surfaces 58 of these subportions to each other. The resulting barrier cuff 62 comprises two layers of backsheet 42 sandwiched between two layers of topsheet 38 and the resulting gasketing cuff 80 comprises one layer of backsheet 42 and one layer of topsheet 38. The portion of the cuff area 102 adjacent each of the first and second ends of the cuff area 122, 124 is joined to the topsheet 38 or underlying structure for a diaper 20 using either of the two folding patterns discussed above.

In the preferred embodiments of both of these folding patterns, the barrier cuff 62 will include a spacing means 76 which is preferably an elasticized member and the gasketing cuff 80 will preferably include an elasticized member 84.

Figure 9:
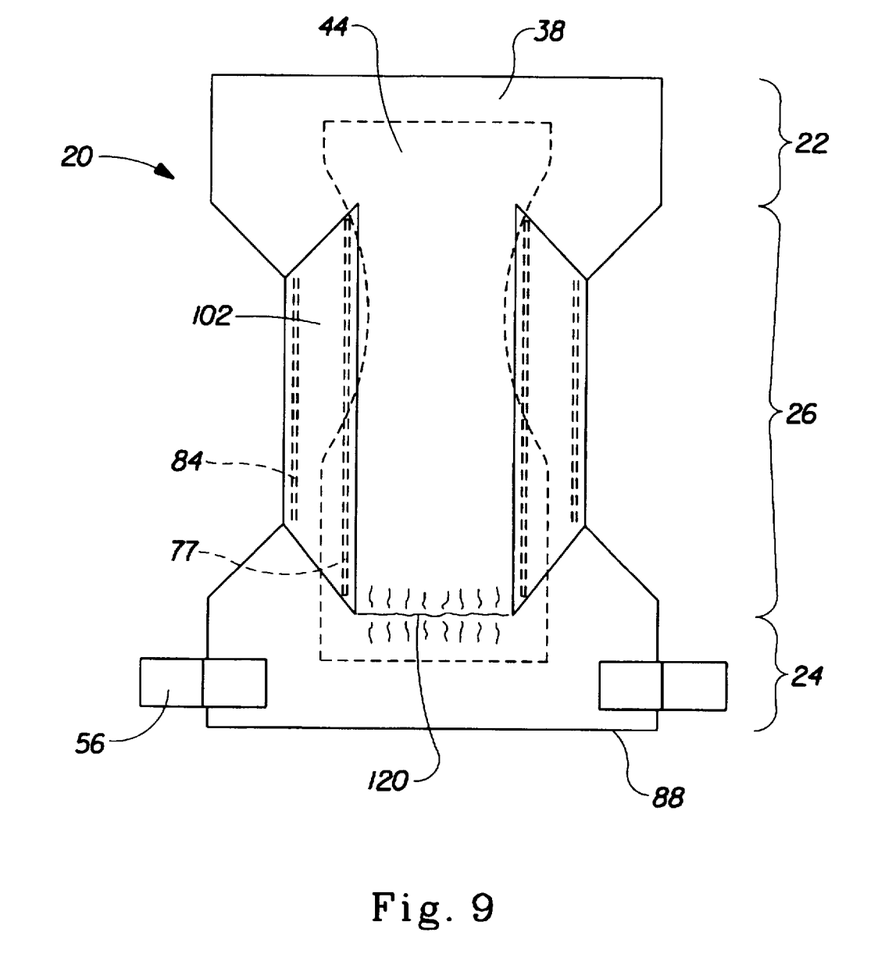
FIG. 9 presents an illustration of an embodiment of this invention including a pocket in the second waist region of the article.

In another embodiment of this article, shown in FIG. 9, when the topsheet 38, backsheet 42 and absorbent core 44 are associated into a chassis, the topsheet 38 remains unjoined to the underlying layers, except at the periphery in at least the second waist region 24. The barrier cuffs 62 are formed by any of the folding patterns described above and joined to the underlying layers, e.g., topsheet 38. In this embodiment, at least the barrier cuffs 62 are elasticized or include elastic-like elements in their distal edges. The contractile forces of the elastic members cause the topsheet 38 to gather and form a pocket in the second waist region 24 which acts to inhibit the flow of a bowel movement out of the second waist region 24 of the diaper 20.

The diaper 20 is preferably applied to a wearer by positioning the second waist region 24 behind the wearer's back and drawing the remainder of the diaper 20 between the wearer's legs so that the first waist region 22 is positioned across the front of the wearer. The ends of the tape tab fasteners 56 are then secured preferably to outwardly facing areas of the diaper 20. In this manner, the barrier cuffs 62 should be disposed in the "no motion" zone of the wearer in the crotch region 26.

The Process:

Having described the product in detail, the process of this invention by which the product is manufactured shall be discussed.

In the method of this invention, a web including a topsheet 38, backsheet 42 and absorbent core 44 is associated for forming a diaper 20 using any conventional fashion. The topsheet 38 and the backsheet 42 are associated together in any suitable manner as is well known in the diaper manufacturing art. As used herein, the term "associated" encompasses configurations in which diaper components are directly joined to each other by affixing one component directly to another component, and configurations whereby one component is indirectly joined to another component by affixing one component to intermediate members which in turn are affixed to the other component. The topsheet 38 and the backsheet 42 can be joined directly to each other in the diaper periphery 28 by an adhesive or any other attachment means as is known in the art. Thus, for example, a uniform continuous layer of adhesive, a patterned layer of adhesive, an array of separate lines or spots of adhesive, or a network of adhesive filaments may be used.

After the web has been formed, it is cut at spaced locations along its longitudinal edges to create a cuff area 102 on each side of the diaper 20. As used herein, the word "cut" means a mechanically disposed line of weakness having an open end and a closed end point and includes fully or partially (e. g., a perforation pattern) severing the web between the open and the closed ends. As shown in FIG. 4, the cuts 104 can be provided in the first waist region 22 of the diaper at approximately the transition point between the crotch region 26 and the first waist region 22. The cuts 104 may be made in the area of the diaper 20 in which side notches are typically made in the current art. Cuts 104 are positioned so that the angle formed by cuts 104, which define the cuff area 102, with the lateral centerline 34 is at least about 0° and no greater than about 70°. Preferably, the cuts 104 in the second waist region 24 will have an angle of about 25° to about 50° with the lateral centerline 34. One skilled in the art will appreciate that the angular relationship between the cuts and the lateral centerline 34 will depend on the size of the article being manufactured and the length of the elastic member 77 desired in the resulting barrier cuffs 62 and gasket cuffs 70. One skilled in the art will also appreciate that the length of cuts 104 also depends on the effective height of the barrier cuffs 62 desired and of the article being manufactured. One skilled in the art will further appreciate that the cuts 104 do not necessarily have to be straight and could also be curved or arcuate. One skilled in the art will further recognize that the cuts 104 could also comprise a line of weakness in the web such as the land areas of a perforation pattern.

Alternatively, one of the cuts can be adjacent the lateral edge 32 in the first waist region 22 to produce a diaper 20 similar to the one shown in FIG. 1. This cut may also serve to sever a finished diaper 20 from the web if the cut, fold, cut process described below is employed. For this embodiment of diaper 20, cuts are provided in the second waist region 24 of the diaper 20 at approximately the transition point between the crotch region 26 and the second waist region 24.

The cuts 104 define two laterally opposed cuff areas 102 one cuff area 102 on each side of the diaper as shown in FIG 4. Each cuff area 102 may have a generally trapezoidal shape with the longer side of the trapezoidal shape being farthest away from the longitudinal centerline 36 of the diaper 20

Each cuff area 102 can be divided into an inner longitudinal portion 106, an outer longitudinal portion 108 and a middle longitudinal portion 110. The specific relationship of the sizes of the portions 106, 108 and 110 determines the size of both the barrier cuffs 62 and the gasketing cuffs 80. The inner longitudinal portion 106 is that portion closest to the longitudinal centerline 36 and coterminous with the closed ends of the cuts 104. The outer longitudinal portion 108 is adjacent the outer longitudinal edge 30 of the web. The middle longitudinal portion 110 is located between the inner longitudinal portion 106 and the outer longitudinal portion 108. Additionally, each cuff area 102 terminates in a first end 122 and a second end 124.

After the cuff areas 102 have been cut, the cuff areas 102 are folded to create the barrier cuffs 62 and the gasketing cuffs 80. To form the barrier cuffs 62 of the diaper 20 shown in FIG. 1, the cuff areas 102 are folded inwardly toward the longitudinal centerline 36 of the diaper 20 and secured to the topsheet 38, or other layer underlying the topsheet, by a bonding means 112. The barrier cuffs 62 are preferably secured at the first and second ends of the cuff area 122 and 124. The resulting cuffs 62 will then stand up in the crotch region 26 when the diaper 20 is applied to the wearer.

A spacing means 76 may optionally be placed in the cuff area 102 before the cuts are made. Preferably, this spacing means 76 is an elastically extensible member and can be placed in one of the longitudinal portions 106, 108 and 110 of the cuff area 102 depending on the desired arrangements of the resulting cuffs 62 and 80. Alternatively, the spacing means may comprise a stiffening member or other member that will cause the barrier cuffs 62 to stand up when the diaper 20 is applied. If the spacing means 76 is included in the outer longitudinal portion 110, then the resulting barrier cuff 62 will be spaced from the liquid receiving surface of the diaper 20. If an elastically extensible element 84 is placed in the inner longitudinal portion 106 or the middle longitudinal portion 108 of the cuff area 102, a contractible gasket cuff 70 will also be formed. Preferably the diaper 20 will include two elastic elements, a spacing means 76 and an elastically extensible element 84. When the spacing means 76 and the elastically extensible element 84 are employed, both a spaced barrier cuff 62 and a contractible gasket cuff 80 will result.

In a second folding pattern for the embodiment of diaper 20 shown in FIG. 1, the longitudinal edges of the web are folded about the spacing means 76 in a first C-fold which also defines the distal edge 66 of the barrier cuff 62. The cuff area 102 is then folded toward the longitudinal centerline 36 and joined to the topsheet or other underlying structure as described above. For this folding pattern the backsheet 42 is preferably narrower than the topsheet 38 so, when the longitudinal edges of the web are folded about the spacing means 76, the portion of the web that is folded about the spacing means comprises only topsheet 38. This process can be used to produce the embodiment of the diaper 20 having the folding pattern shown in FIG. 2.

Figure 3:
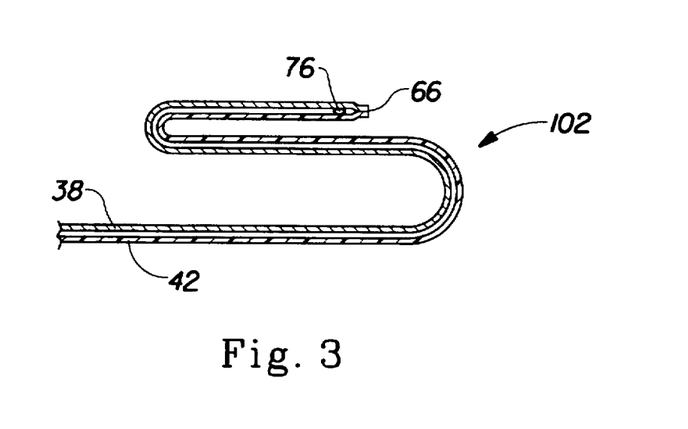
FIG. 3 presents a partial cross section of the cuff area to illustrate alternative folding pattern for the absorbent article shown in FIG. 1.

The diaper 20 having the folding pattern shown in FIG. 3 can be produced with the following variation of the process described above. The cuff area 102 is folded toward the longitudinal centerline 36 in a first C-fold and the first and second ends of the cuff area 122, 124 are joined to the topsheet 38 or other underlying structure in the first and second waist regions as described above. However, in this embodiment, the ends of the cuff area are joined to the first and second waist areas inboard of the distal edge 66 leaving a portion of the cuff area 102 unattached. This unattached portion is folded away from the longitudinal centerline 36 in a second C-fold and the first and second ends of this unattached portion of the cuff area 102 are then joined to underlying structure in the first and second waist regions 22, 24.

Preferably a cut, fold, cut process is used to produce the diaper 20 shown in FIG. 1. This process allows improved ease of processing yet provides a diaper 20 that can be easily opened by a consumer. In this process two laterally opposed first cuts 104 are made in the web. In this embodiment of the process, the first cuts 104 comprise a perforation pattern and define the junction between the second waist region 24 and the crotch region 26. Preferably, the perforation pattern comprises at least two land areas having a minimum length of 1 mm (0.040 inches). The web is then folded toward the longitudinal centerline and joined to the topsheet or other underlying layers as described above. A second cut 104 is then made that is juxtaposed with the lateral edge 32 that is in the first waist region 22. This second cut both completes definition of the cuff area 102 and severs an individual diaper 20 from the web.

In a third folding pattern of this invention, as shown in FIGS. 5A and 5B the web is provided and the cuts 104 are made as described above. After the cuts 104 are made, a bonding means 112 is utilized adjacent a line connecting the closed ends of the cuts to join the inner longitudinal portion 106 to the underlying layers as shown in FIG. 5A. The bonding means 112 may be any means for securing the cuff area 102 to the topsheet 38 such as adhesives, heat/pressure sealing, ultrasonic bonding, or any other means or methods as are known in the art. For example, adhesives can be applied to the topsheet 38, or any layer underlying the topsheet 38, adjacent to and on the side inboard of a line extending between the ends of cuts 104.

The cuff area 102 is then folded inwardly toward the longitudinal centerline 36 of the diaper 20 and joined to the topsheet 30 or other layer underlying the topsheet 38. The cuff area 102 is folded along a line between the cuts 104 so that the inner longitudinal portion 106 becomes attached to the topsheet 38 or other layer underlying the topsheet 38 of the diaper 20. The middle longitudinal portion 110 and the outer longitudinal portion 108 are then folded away from the centerline 36 of the diaper 20 to form the barrier cuffs 62.

After the cuffs have been formed, the portion of the cuff area 102 adjacent the cuts, i. e. adjacent the ends of the cuff area 122, 124, is attached to the underlying portions in the first and second waist regions 22 and 24. This creates a barrier cuff 62 which is unattached to the diaper 20 in the crotch region 26 and which will stand up in the crotch region 26 when the diaper is applied to a wearer. The resulting diaper 20 will have a barrier cuff 62 consisting of a single ply of both topsheet and backsheet and a gasketing cuff 80 consisting of two layers of both topsheet and backsheet, as seen in FIG. 5B. One skilled in the art will appreciate that the dimensions of both the barrier cuff 62 and the gasketing cuff 80 can be varied depending on what proportion of the cuff area is folded inwardly toward the longitudinal centerline and the depth to which the cuts 104 are made in the diaper 20.

Figure 7:
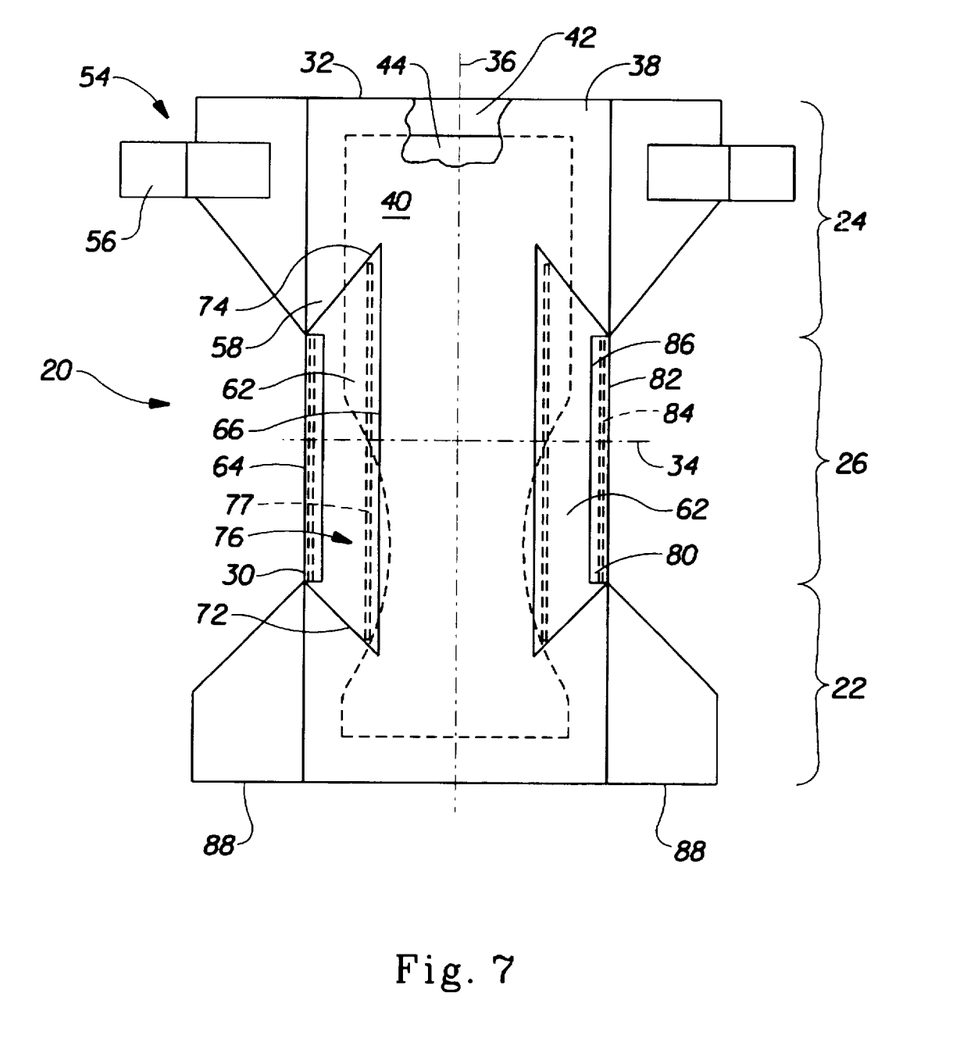
FIG. 7 presents an illustration of an alternate embodiment of the article of this invention.

In the embodiment shown in FIG. 7, the ends of barrier cuffs 62 are attached to the topsheet 38 with the distal edge 66 of each barrier cuff 62 directed inwardly toward the longitudinal centerline 36 of the diaper 20. In an alternate embodiment, the ends of the barrier cuffs 62 can be attached to the topsheet 38 with the distal edge 66 of each cuff 62 directed outwardly from the centerline 36 in both the first and second waist regions 22 and 24 of the diaper 20. The barrier cuffs 62 may also be "inflected", i.e. one end may be joined to underlying layers, e.g., the topsheet 38, toward the longitudinal centerline 36 and the other end may be joined to the topsheet 38 outboard of the proximal edge 64 of the cuff 62.

As shown in FIGS. 6A and 6B, in a fourth folding pattern, the topsheet 38, backsheet 42 and absorbent core 44 are associated into a diaper web, as described above. The diaper web is then cut, also as described above, to form the cuff areas 102. The cuff area 102 is first folded toward the longitudinal centerline 36 along a line extending between the inside ends of the cuts 104. The cuff area 102 is then folded longitudinally in the middle longitudinal portion 110 away from the longitudinal centerline 36 to form two subportions. The garment facing surfaces 58 of these subportions are then joined using bonding means 112. For example, as shown in FIG. 6A, a bonding means 112 is utilized adjacent the fold in middle longitudinal portion 110 on the garment facing surface of the cuff area 102 to join the folded over portions to each other. As seen in FIG. 6B, this method creates a barrier cuff 62 consisting of two plies each of topsheet and backsheet material and a gasketing cuff 80 having one ply of topsheet and backsheet material. The ends of the outer longitudinal portion 108 of the cuff area 102 are then attached to the topsheet 38 by a bonding means 112, as described above, to complete construction of the gasketing cuffs 80.

In an alternate embodiment of the process described above, shown in FIG. 7, a backsheet 42, which is laterally narrower than the topsheet 38 is employed. This creates a web in which the topsheet 38 extends beyond the edges of the backsheet 42, preferably for an equal distance, on each side of the web. For example, the backsheet 42 may have a lateral width which is approximately one to five inches smaller than the lateral width of the topsheet 38. The barrier cuffs 62 may be formed by any of the folding patterns described above. However, the folding pattern, as described in FIGS. 6A and 6B, is preferred because, depending upon the width of the backsheet 42, it results in a barrier cuff 62 having outer plies of topsheet and at least a single inner ply of backsheet which helps to prevent leaking through the barrier cuff, and in a gasketing cuff 80 comprising only topsheet. This produces a diaper having soft gasketing cuffs 80.

If the backsheet is folded according to the folding pattern shown in FIGS. 5A and 5B, a gasketing cuff 80 having one outer ply and one inner ply of topsheet material and one outer ply of backsheet material would result. This second embodiment would provide a moisture pervious gasketing cuff 80. However, this folding pattern would produce a barrier cuff 62 which would be permeable by liquids thus increasing the risk of leaks. To prevent the barrier cuff 62 formed by the second embodiment from leaking, the barrier cuff 62 must be impermeable to liquids. For example, depending on the wettability of the topsheet material, a treatment may be necessary to make those portions of the topsheet which overlie the absorbent core hydrophilic and those portions which are laterally outboard of the absorbent core hydrophobic. Such treatments may be applied by the supplier of the topsheet material or as an additional step in the manufacturing process to render the resulting barrier cuff 62 impermeable to liquids.

In the alternative embodiment of the process described above, the topsheet 38 is secured to the backsheet 42 only in the periphery of the diaper in the second waist region 24. The diaper web is formed as described above except that the topsheet 38 is not secured to the absorbent core 44 in the second waist region 24 but is secured at the end edges 32 and longitudinal sides 30 in the second waist region 24. The cuff area 102 is then cut and the attached to the body of the diaper 20 in any of the manners described above. In this embodiment, it is preferred that the distal edges 66 of the resultant barrier cuffs 62 be elasticized and be directed inwardly toward the longitudinal centerline 36. A diaper 20 resulting from this alternative process is shown in FIG. 9. As shown in FIG. 9, the retractile forces of the elastic elements 77 of the leg cuff 62 act to form a pocket 120 in the second waist region 24 by raising the topsheet 38 off of the underlying layers. This process results in a barrier which restricts the flow of runny bowel movements out of the second waist region 24 of the diaper 20.

Figure 8:
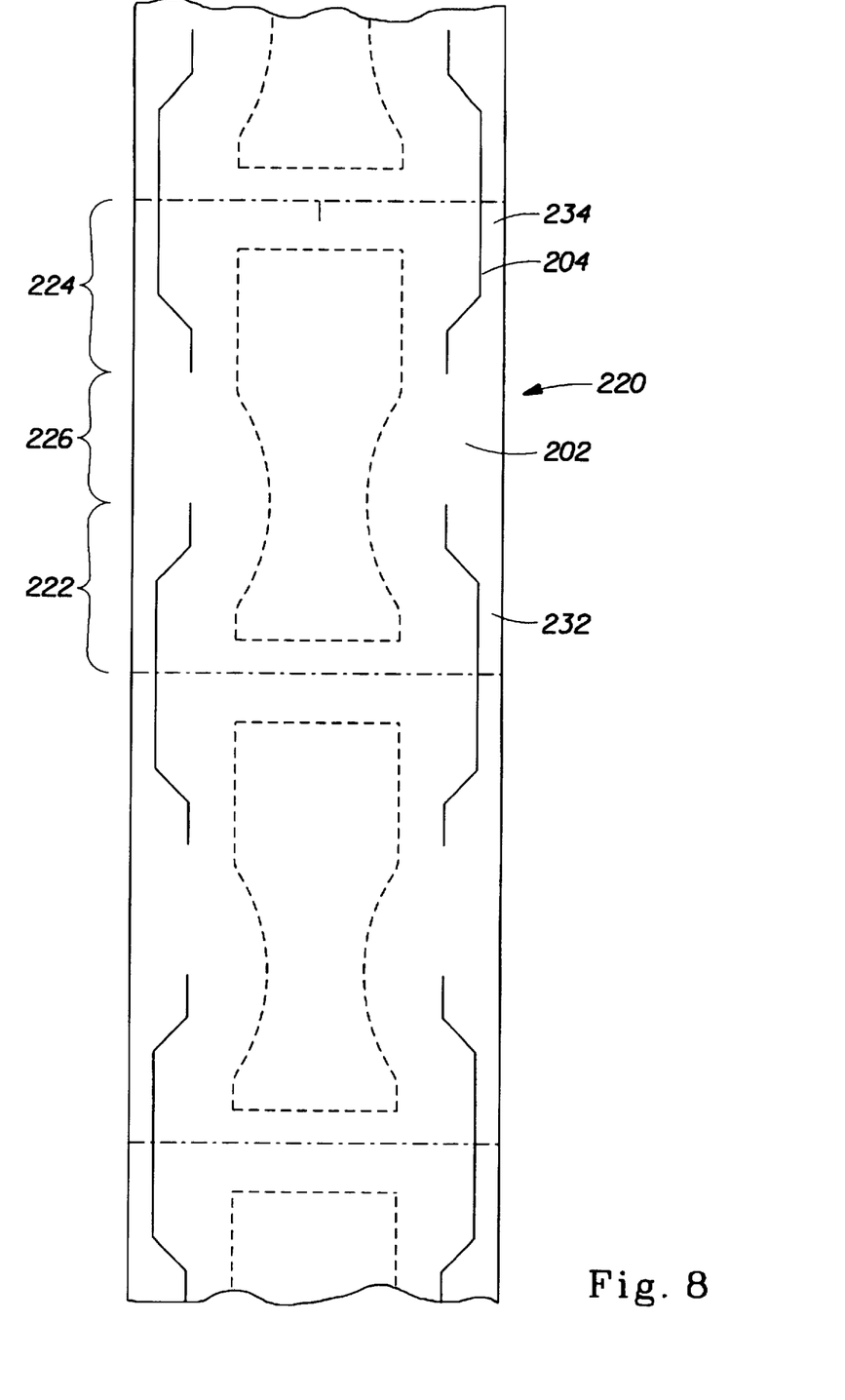
FIG. 8 presents an illustration of an embodiment of the process of this invention in which the cuff area is created by continuous cuts from one article to the next.

For any of the embodiments described above, the cuts 204 may also be continuous from one portion of the web to the next, as shown in FIG. 8. Although the diaper web is not cut into individual diapers until the end of the process, the web can be divided into separate articles for purposes of illustration. By "continuous", it is meant that the cut 204 begins in the first waist region 222 of a first diaper 220 and continues into the second waist region 224 of the following diaper 220 in the web. In this cutting process, no cuts are made in the crotch region 226 of the articles. If the cuts 204 are made continuously from one diaper 220 to the next, the resulting cuff area 202 will have a first trailing end 232 and a second trailing end 234 at first end 222 and second end 224, respectively. The cuff area 202 is then folded to form a barrier cuff (not shown) in any of the manners described above. The first and second trailing ends 232 and 234 are secured to the topsheet to complete the formation of the barrier cuffs. One skilled in the art will appreciate that these first and second trailing ends 232 and 234 may be trimmed to any desired length before affixing them to the topsheet.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent article having a longitudinal centerline, a lateral centerline, longitudinal side edges and lateral ends defining a periphery, a first waist region, a second waist region and a crotch region between the first waist region and the second waist region, and comprising:

a liquid pervious topsheet;

a liquid impervious backsheet joined to the topsheet;

an absorbent core having longitudinal side edges disposed between the topsheet and the backsheet;

a pair of longitudinally extending barrier cuffs, each of the barrier cuffs being integrally formed from a lateral extension of the topsheet and the backsheet beyond the side edge of the absorbent core, the lateral extension being provided with first and second cuts defining a cuff area having first and second ends, the cuff area further having a free distal edge, the distal edge being folded toward the longitudinal centerline, at least one of the ends of the cuff area being joined to one of the first waist region or the second waist region to form the barrier cuff, each of the barrier cuffs being further provided with a spacing means adjacent the distal edge for spacing the barrier cuffs upwardly away from the absorbent core in at least the crotch region; and a pair of longitudinally extending gasketing cuffs integrally formed from the extended topsheet and backsheet and lying laterally outboard of the barrier cuff in at least the crotch region.

2. The absorbent article of claim 1 wherein the barrier cuffs are formed of one layer of topsheet and one layer of backsheet and the gasketing cuffs are formed of two layers of topsheet sandwiched between two layers of backsheet.

3. The absorbent article of claim 1 wherein the barrier cuffs are formed of two layers of backsheet sandwiched between two layers of topsheet and the gasketing cuffs are formed of one layer of backsheet and one layer of topsheet.

4. The absorbent article of claim 2 wherein the spacing means comprises an elastic member.

5. The absorbent article of claim 3 wherein the spacing means comprises an elastic member.

6. The absorbent article of claim 1 wherein the backsheet has a lateral width that is narrower than the topsheet so that the barrier cuffs consist of one layer of backsheet sandwiched between two layers of topsheet and the gasketing cuffs consist only of topsheet.

7. The absorbent article of claim 1 wherein at least one of the cuts comprises a perforation pattern.

8. The absorbent article of claim 1 wherein the first and second ends of the barrier cuffs are attached to the topsheet so that the distal edges of the barrier cuffs are directed inwardly toward the longitudinal center line.

9. The absorbent article of claim 6 wherein the spacing means is elastic and the gasketing cuff further includes an elastic member.

10. The absorbent article of claim 9 wherein the topsheet is folded about the elastic member in a C-fold.

11. A method for making an absorbent article having barrier leg cuffs, a first waist region, a second waist region, a crotch region disposed between the first and second waist regions, a longitudinal centerline, and a pair of opposed longitudinal side edges comprising the steps of:

providing a web having side edges, the web comprising a fluid pervious topsheet, a fluid impervious backsheet, an absorbent core disposed between the topsheet and the backsheet, the absorbent core having side edges and waist edges, and at least one elastic member disposed adjacent each side edge of the web;

cutting the web to provide a pair of laterally opposed cuts along the side edges of the web, the cuts comprising a perforation pattern having a predetermined length inboard of the side edge of the web which defines a closed end of the cut;

folding each side edge of the web toward the longitudinal centerline adjacent a line connecting the closed ends of the cuts on the side of the web where the cuts are located to form a folded portion on each side of the web;

providing first and second longitudinally spaced apart attachment means to join the folded portion on each side of the web to underlying portions of the web, one first attachment means being adjacent each cut and the second attachment means being a predetermined longitudinal distance away the first attachment means; and severing the web adjacent the second attachment means to form the absorbent article.

12. An absorbent article having a longitudinal centerline, a lateral centerline, longitudinal side edges and lateral ends defining a periphery, a first waist region, a second waist region and a crotch region between the first waist region and the second waist region, and comprising:

a liquid pervious topsheet;

a liquid impervious backsheet joined to the topsheet;

an absorbent core having longitudinal side edges disposed between the topsheet and the backsheet;

an elastic waist feature in the second waist region;

elasticized ear panels in the second waist region having side edges which extend laterally outwardly beyond the side edges of the absorbent core;

fastening means disposed on the waist feature for forming a closure in the absorbent article; and a pair of longitudinally extending barrier cuffs, each of the barrier cuffs being integrally formed from a lateral extension of the topsheet and the backsheet beyond the side edge of the absorbent core, the lateral extension being provided with first and second cuts defining a cuff area having first and second ends, the cuff area further having a free distal edge, the distal edge being folded toward the longitudinal centerline in a C-fold, one of the ends of said cuff area being joined to said first waist region and the other of the ends of the cuff area being joined to the second waist region to form the barrier cuff, each of the barrier cuffs being further provided with a spacing means adjacent the distal edge for spacing the barrier cuffs upwardly away from the topsheet in at least the crotch region wherein the backsheet is narrower than the topsheet, the spacing means comprises an elastic member adjacent the distal edge of the cuff area, and the top sheet is folded about the elastic member in a C-fold.

13. The absorbent article of claim 12 wherein the cuff area is divided into first and second longitudinal portions, the first longitudinal portion being adjacent said longitudinal side edge of the absorbent core and the second longitudinal portion being adjacent the distal edge, the distal edge being folded away from the longitudinal centerline in a second C-fold and the first portion of the cuff area being joined to the second portion of the cuff area in each of the first and second waist regions.

14. A method of making a disposable absorbent article having barrier cuffs, a first waist region, a second waist region, a crotch region disposed between the first and second waist regions, a longitudinal centerline, and a pair of opposed longitudinal side edges comprising the steps of:

providing a web comprising a fluid pervious topsheet, a fluid impervious backsheet, an absorbent core disposed between the topsheet and the backsheet, the absorbent core having side edges and waist edges, and at least one elastic member disposed between the topsheet and the backsheet adjacent each side edge of the absorbent core;

making at least one pair of laterally opposed cuts along the side edges of the web, at least one of the cuts having an opened end and a closed end, each pair of cuts defining a cuff area which extends from the closed end outwardly to the longitudinal side edge of the web, the cuff area including an inner longitudinal portion being coterminous with the closed ends of the cuts, a middle longitudinal portion, and an outer longitudinal portion, each cuff area having a body facing surface, a garment facing surface, and first end and a second end; and attaching the first and second ends of the cuff area to the topsheet so that a barrier cuff having a distal edge which is unattached to the topsheet in at least the crotch region results, wherein said step of attaching further comprises the steps of:

providing a first means for bonding in the first and second waist regions of the article on either side of a line extending between the closed ends of the cuts;

making a first fold, along a line conterminous with the closed ends of the cuts, toward the longitudinal centerline so that the first means for bonding secures a portion of the inner longitudinal portion to the topsheet in each of the first and second waist regions and the remainder of the inner longitudinal portion remains unattached in the crotch region;

providing a second means for bonding on the garment facing surface of the folded over cuff area in either the inner or middle longitudinal portions;

providing a third means for bonding on the topsheet adjacent the cut lines in the first and second waist regions of the web;

making a second longitudinal fold in the middle longitudinal portion of the cuff area away from the longitudinal centerline so that the second means for bonding attaches the cuff area to itself in the middle longitudinal portion; and attaching the first and second ends of the outer longitudinal portion of the cuff area to the topsheet in the first and second waist regions by a third means for bonding to produce gasketing cuffs each having a distal edge, wherein the backsheet is laterally narrower than the topsheet so that the barrier cuffs each comprise two layers of topsheet material and a center layer of backsheet material and the gasketing cuffs each comprise only topsheet material.

15. The method of claim 14 wherein the absorbent article includes two elastic members disposed between the topsheet and the backsheet, a first elastic member being adjacent each side edge of the absorbent article and a second elastic member being located between each first elastic member and the absorbent core.

16. A method of making a disposable absorbent article having barrier cuffs, a first waist region, a second waist region, a crotch region disposed between the first and second waist regions, a longitudinal centerline, and a pair of opposed longitudinal side edges comprising the steps of:

providing a web comprising a fluid pervious topsheet, a fluid impervious backsheet, an absorbent core disposed between the topsheet and the backsheet, the absorbent core having side edges and waist edges, and at least one elastic member disposed between the topsheet and the backsheet adjacent each side edge of the absorbent core;

making at least one pair of laterally opposed cuts along the side edges of the web, at least one of the cuts having an opened end and a closed end, each pair of cuts defining a cuff area which extends from the closed end outwardly to the longitudinal side edge of the web, the cuff area including an inner longitudinal portion being coterminous with the closed ends of the cuts, a middle longitudinal portion, and an outer longitudinal portion, each cuff area having a body facing surface, a garment facing surface, a first end and a second end;

attaching the first and second ends of the cuff area to the topsheet so that a barrier cuff having a distal edge which is unattached to the topsheet in at least the crotch region results, wherein said step of attaching further comprises the steps of:

providing a means for bonding longitudinally adjacent to either side of a line extending between the closed ends of the cuts in the crotch region;

folding toward the longitudinal centerline so that the means for bonding attaches the inner longitudinal portion to the topsheet in at least the crotch region;

making a second longitudinal fold in the middle longitudinal portion of the cuff area away from the longitudinal centerline; and attaching the ends of the cuff area to the topsheet in at least the first and second waist regions so that the cuff area remains unattached forming the barrier cuffs in the crotch region and so that the portion of the cuff areas adjacent to the longitudinal edges of the web forms gasketing cuffs, each having a distal edge.

17. The method of claim 16 wherein the step of attaching the cuff area to the topsheet comprises the steps of:

providing a means for bonding longitudinally adjacent to either side of a line extending between the closed ends of the cuts in the crotch region;

folding toward the longitudinal centerline so that the means for bonding attaches the inner longitudinal portion to the topsheet in at least the crotch region;

making a second longitudinal fold in the middle longitudinal portion of the cuff area away from the longitudinal centerline; and attaching the ends of the cuff area to the topsheet in at least the first and second waist regions so that the cuff area remains unattached forming the barrier cuffs in the crotch region and so that the portion of the cuff areas adjacent to the longitudinal edges of the web forms gasketing cuffs, each having a distal edge.

* * * * *